United States Patent [19]

Farooque

[11] Patent Number: 4,772,634
[45] Date of Patent: Sep. 20, 1988

[54] APPARATUS AND METHOD FOR METHANOL PRODUCTION USING A FUEL CELL TO REGULATE THE GAS COMPOSITION ENTERING THE METHANOL SYNTHESIZER

[75] Inventor: Mohammad Farooque, Huntington, Conn.

[73] Assignee: Energy Research Corporation, Danbury, Conn.

[21] Appl. No.: 892,246

[22] Filed: Jul. 31, 1986

[51] Int. Cl.[4] .................... C07C 27/06; B01J 8/00
[52] U.S. Cl. ......................... 518/704; 422/188; 422/189; 429/17
[58] Field of Search .............. 518/704; 422/187–189; 429/17–19

[56] References Cited

U.S. PATENT DOCUMENTS

| | | | |
|---|---|---|---|
| 3,266,938 | 8/1966 | Parker et al. | 429/17 |
| 3,585,078 | 6/1971 | Sederquist et al. | 429/17 |
| 3,615,850 | 10/1971 | Lynn et al. | 429/17 |
| 3,785,870 | 1/1974 | Winsel | 429/17 |
| 3,909,299 | 9/1975 | Corrigan | 422/190 |
| 4,002,805 | 1/1977 | Waldman | 429/17 |
| 4,080,791 | 3/1978 | Nadler et al. | 429/12 |
| 4,309,359 | 1/1982 | Pinto | 48/197 R |
| 4,349,613 | 9/1982 | Winsel | 429/17 |
| 4,522,894 | 6/1985 | Hwang et al. | 429/17 |

Primary Examiner—Barry S. Richman
Assistant Examiner—Timothy M. McMahon
Attorney, Agent, or Firm—Robin, Blecker & Daley

[57] ABSTRACT

Methanol production is realized by utilizing a fuel cell to control the gas composition of the synthesis gas stream being fed to the methanol synthesizer.

11 Claims, 1 Drawing Sheet

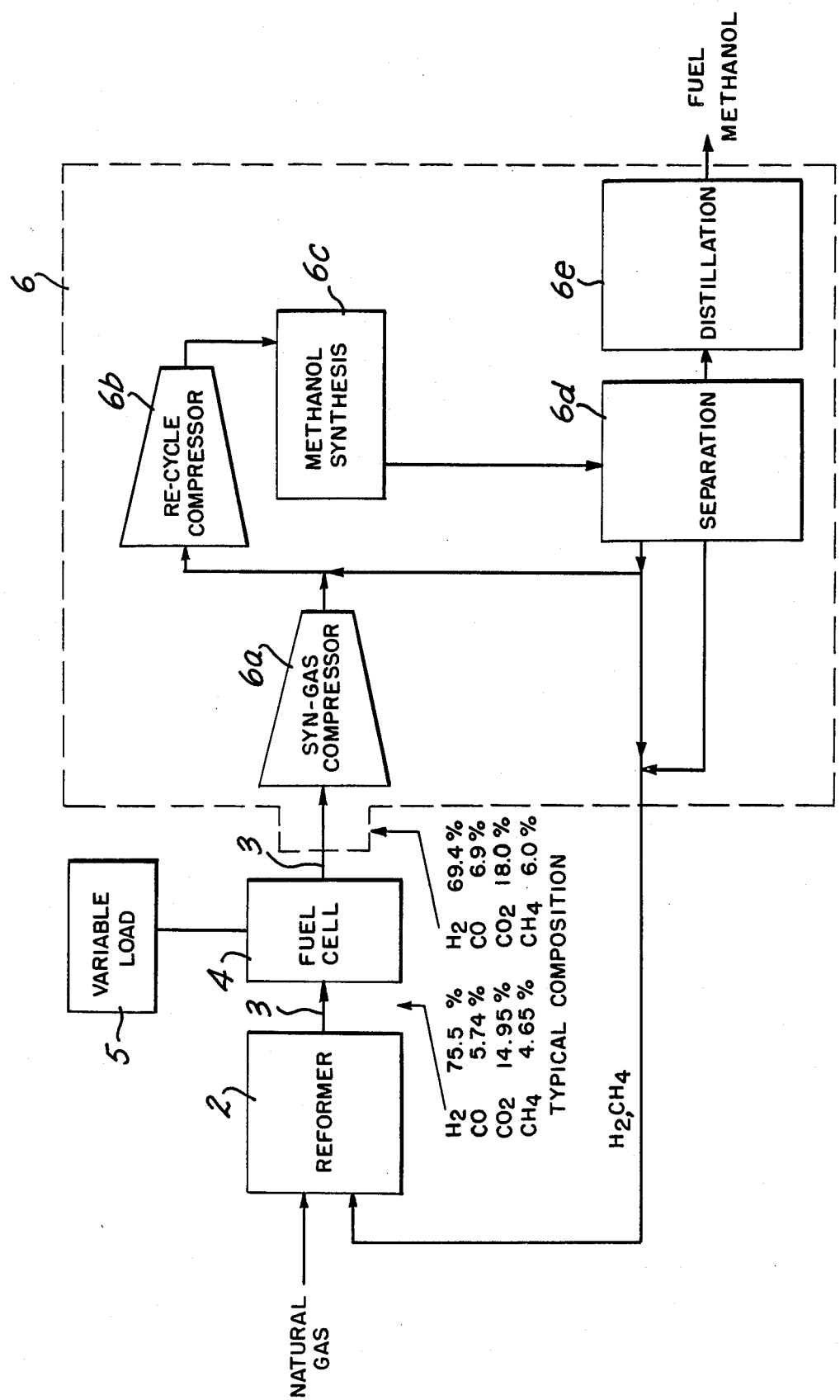

APPARATUS AND METHOD FOR METHANOL PRODUCTION USING A FUEL CELL TO REGULATE THE GAS COMPOSITION ENTERING THE METHANOL SYNTHESIZER

BACKGROUND OF THE INVENTION

This a method and apparatus for producing methanol and, in particular, to a method and apparatus for producing methanol using a synthesis gas.

In present day methanol production, the low pressure methanol synthesis process (50–100 atm.; 200°–300° C.), available since the 1960's, is universally favored over the high pressure process (250–350 atm.; 350°–450° C.). In the low pressure porcess, a feedstock having hydrocarbon content, e.g., natural gas, coal, heavy oils, naptha, propane or butane, is first reformed to produce a gas stream rich in hydrogen. This hydrogen-rich gas stream is then adjusted in composition and the resultant stream containing hydrogen, carbon dioxide and carbon monoxide catalytically synthesized to produce the desired methanol.

Usually, the reformation process results in a synthesis gas whose hydrogen content is greater than that needed for the methanol reaction. This excess hydrogen may be used as fuel in the plant or may be cryogenically separated from the synthesis gas stream and used in other applications. Also, $CO_2$ may be added to the synthesis gas stream to convert some of the hydrogen to CO. This procedure adjusts the stoichiometric number expressed by equation (a) below to the desired value, $$\frac{H_2 - CO_2}{CO_2 + CO} \quad (a)$$

thereby increasing the methanol yield. However, the $CO_2$ added to the gas stream is generally recovered from the reformer flue which is a costly process.

While the above procedures have thus been successfully utilized for methanol production, other procedures which could result in reduced cost are still being sought.

It is, therefore, an object of the present invention to provide an apparatus and method for methanol production.

It is a further object of the present invention to provide a method and apparatus for methanol production utilizing unique means for adjusting the hydrogen content of the synthesis gas.

SUMMARY OF THE INVENTION

In accordance with the principles of the present invention the above and other objectives are realized by passing the hydrogen-rich synthesis gas through a fuel cell which is adapted to add a preselected quantity of $CO_2$ to the gas stream and/or consume a preselected portion of the hydrogen in the gas stream as fuel gas. The gas stream with reduced hydrogen content and its stoichiometric number adjusted to the desired value is then fed to a methanol synthesizer which forms methanol from the gas stream products.

With the present invention, the hydrogen consumed in the fuel cell is readily adjusted and controlled by adjusting the load and, therefore, the current of the cell. As a result, the composition or makeup of the gas stream leaving the cell can be precisely adjusted and controlled so as to provide a gas stream for the synthesizer having the desired stoichiometric number. Also, the electrical output of the fuel cell can be used as an electrical energy source so that the hydrogen removal process is carried out in a manner which results in maximum usage of energy.

BRIEF DESCRIPTION OF THE DRAWING

The above and other features and aspects of the present invention will become more apparent upon reading the following detailed description in conjunction with the accompanying drawings in which the sole FIGURE illustrates a system for producing methanol in accordance with the principles of the present invention.

DETAILED DESCRIPTION

In the FIGURE, hydrocarbon feedstock, shown as natural gas, is fed into a reformer 2 which converts the feedstock into a gas stream 3 which is rich in hydrogen and which also contains carbon dioxide, carbon monoxide and unreacted methane. The reformer 2 may be a conventional steam reformer or gasifier, depending upon the hydrocarbon feedstock.

The gas stream 3 is then fed into a fuel cell 4 which drives a variable load 5. A portion of the hydrogen in the stream 3 is utilized as fuel by the fuel cell 4 and/or $CO_2$ is added to the stream by the fuel cell, so that the stream 3 passes from the fuel cell 4 with an increased $CO_2$ content and/or a reduction in its hydrogen content.

The stream 3 is then coupled into a conventional methanol synthesizer 6 wherein the stream is converted into methanol. As shown, synthesizer 6 includes a syngas compressor 6a which receives the stream 3 from the fuel cell 4. The output of the compressor 6a is coupled to a recycle compressor 6b and from the compressor 6b to a methanol synthesis unit 6c.

The output of the unit 6c is coupled to a separation apparatus 6d which separates the produced methanol from the other constituents in the unit 6c output. The separated methanol is then passed to a distillation unit 6e and from there out of the synthesizer 6.

Portions of the other constituents (hydrogen and $CH_4$) in the unit 6c output are re-cycled back to the reformer 2 and the re-cycle compressor 6b, respectively. Added to the former portion is an additional output of the separation unit.

As can be appreciated, by controlling the current drawn from the fuel cell 4 with the variable load 5, the gas composition of the stream 3 as it leaves the fuel cell 4 can be precisely controlled. As a result, the stoichiometric number of the stream 3 fed to the synthesizer 6 can also be precisely controlled to that desired for the methanol synthesis process. In the FIGURE, typical compositions of the gas stream 3 entering and exiting the fuel cell 4 are shown for realizing a stoichiometric number of about 2, which is desired for methanol processing in synthesizer 6.

The fuel cell 4 can be a phosphoric acid fuel cell in which case about twenty-five percent of the hydrogen in the gas stream 3 can be consumed to provide the above-mentioned stoichiometric number. In such case, a 104 MW size phosphoric acid fuel cell will be required for a 3000 ton/day methanol plant.

The fuel cell 4 may also be a molten carbonate fuel cell. With this type of cell, hydrogen is removed and $CO_2$ is simultaneously added to the stream 3, as the stream passes through the cell. The addition of each molecule of $CO_2$ to the stream is equivalent to the consumption or removal of two hydrogen molecules. As a result, less hydrogen molecules need to be consumed by the cell 4 to realize the same stoichiometric number. This, in turn, allows more hydrogen to be in the stream 3 entering the synthesizer 6 and, as a result, more methanol to be produced.

In all cases, it is understood that the above-identified arrangements are merely illustrative of the many possible specific embodiments which represent applications of the present invention. Numerous and varied other arrangements can readily be devised in accordance with the principles of the present invention without departing from the spirit and scope of the invention.

What is claimed is:

1. Apparatus for methanol production comprising:
   means for receiving a hydrocarbon feed and for producing therefrom a synthesizer feed gas containing hydrogen, carbon dioxide and carbon monoxide;
   fuel cell means following said reformer means for receiving the synthesizer feed gas from said reformer means and for consuming as fuel a preselected portion of the hydrogen in the synthesizer feed gas to realize a desired value for the stoichiometric number of the synthesizer feed gas;
   and methanol synthesis means following said fuel cell means for receiving the synthesizer feed gas from said fuel cell means and for producing methanol gas therefrom 2. Apparatus in accordance with claim 1 wherein:
   said fuel cell means is a phosphoric acid fuel cell.

3. Apparatus in accordance with claim 1 wherein:
   said fuel cell means is a molten carbonate fuel cell, said fuel cell consuming as fuel as a preselected portion of the hydrogen in the synthesizer feed gas and adding carbon dioxide to the synthesizer feed gas upon passage of the synthesizer feed gas through said cell to realize a desired value for the stoichiometric number of the synthesizer feed gas.

4. Apparatus in accordance with claim 1 further comprising:
   a variable load drawing current from said fuel cell means;
   and means for adjusting said load so that the current drawn results in the consumption of a preselected portion of the hydrogen gas.

5. Apparatus in accordance with claim 1 wherein:
   said fuel cell means is a molten carbonate fuel cell, said fuel cell consuming as fuel a preselected portion of the hydrogen in the synthesizer feed gas or adding carbon dioxide to the synthesizer feed gas upon passage of the synthesizer feed gas through said cell to realize a desired value for the stoichiometric number of the synthesizer feed gas.

6. A method of producing methanol comprising:
   reforming a hydrocarbon feed to produce a synthesizer feed gas containing hydrogen, carbon dioxide and carbon monoxide;
   consuming a preselected portion of the hydrogen in the synthesizer feed gas by passing the synthesizer feed gas through a fuel cell which utilizes a preselected portion of hydrogen in the synthesizer feed gas as fuel;
   processing the synthesizer feed gas after passage through said fuel cell to produce methanol from the synthesizer feed gas.

7. A method in accordance with claim 6 wherein:
   said fuel cell is a phosphoric acid fuel cell.

8. A method in accordance with claim 6 wherein:
   said fuel cell is a molten carbonate fuel cell, said fuel cell adding carbon dioxide to the synthesizer feed gas upon passage of the synthesizer feed gas through said cell.

9. A method in accordance with claim 6 further comprising:
   adjusting a variable load fed by said fuel cell to cause said fuel cell to consume a preselected amount of hydrogen.

10. A method in accordance with claim 6 wherein:
    the preselected portion of hydrogen consumed in said consuming step in such as to realize a desired value for the stoichiometric number of the synthesizer feed gas.

11. Method in accordance with claim 10 wherein:
    said stoichiometric number is about 2.

* * * * *

UNITED STATES PATENT AND TRADEMARK OFFICE
CERTIFICATE OF CORRECTION

PATENT NO. : 4,772,634

DATED : September 20, 1988

INVENTOR(S) : Mohammad Farooque

It is certified that error appears in the above-identified patent and that said Letters Patent is hereby corrected as shown below:

Col. 1, line 8, after "This" insert -- invention relates to --

Col. 3, line 16, before "means" insert -- reformer --

Col. 3, line 34, delete "as" second occurrence.

Col. 4, line 38, change "in" to -- is --

Signed and Sealed this

Twenty-first Day of February, 1989

Attest:

DONALD J. QUIGG

*Attesting Officer*  *Commissioner of Patents and Trademarks*